United States Patent [19]
Palleni

[11] 3,964,476
[45] June 22, 1976

[54] RESPIRATION SYSTEM AND DEVICE

[76] Inventor: Roberto Palleni, 18, Villaggio Aurelia, 20060 Cassina de' Pecchi, Italy

[22] Filed: Nov. 5, 1974

[21] Appl. No.: 521,148

[30] Foreign Application Priority Data
Nov. 5, 1973 Italy .................................. 30902/73

[52] U.S. Cl. ............................ 128/145.6; 417/394
[51] Int. Cl.² ........................................ A61M 16/00
[58] Field of Search ..................... 128/145.5–145.8, 128/142, 142.3, 188, 191 R, 203, 202, 210, 211; 417/394

[56] References Cited
UNITED STATES PATENTS

| | | | |
|---|---|---|---|
| 1,835,157 | 12/1931 | Heidbrink | 128/203 |
| 2,834,339 | 5/1958 | Bennett et al. | 128/145.7 |
| 3,156,238 | 11/1964 | Bird et al. | 128/145.5 |
| 3,467,092 | 9/1969 | Bird et al. | 128/145.6 |
| 3,526,223 | 9/1970 | Curtis | 417/394 |
| 3,537,450 | 11/1970 | Fox | 128/145.6 |
| 3,604,016 | 9/1971 | Robinson | 417/394 |
| 3,865,106 | 2/1975 | Palush | 128/145.8 |
| 3,874,378 | 4/1975 | Isaacson et al. | 128/145.8 |

FOREIGN PATENTS OR APPLICATIONS
1,256,024 2/1961 France ............................ 128/145.7

*Primary Examiner*—Robert W. Michell
*Assistant Examiner*—Henry J. Recla
*Attorney, Agent, or Firm*—Michael J. Striker

[57] ABSTRACT

There is described a respiration device designed to be associated to and operated with a respiration system including a source of pressurized gaseous mixture volumes which are to be cyclically and forcedly supplied into a patient's respiratory system, and a source of pulsing alternated positive and negative pressure. The device comprises an outer tubular component having inextensible walls and an inner hose having squashable walls, and inlet and outlet valves at either ends connected to the source of gaseous mixture and to a face mask or tracheal tube or the like, respectively, the source of pulsing pressure being connected to the interspace between said component and said hose, so that the latter acts a variable volume chamber for supplying one gaseous volume at any inhalation phase of the breathing cycle when the hose is squashed by the pressure applied thereabout in said interspace, the outlet valve being located very near to the patient.

10 Claims, 6 Drawing Figures

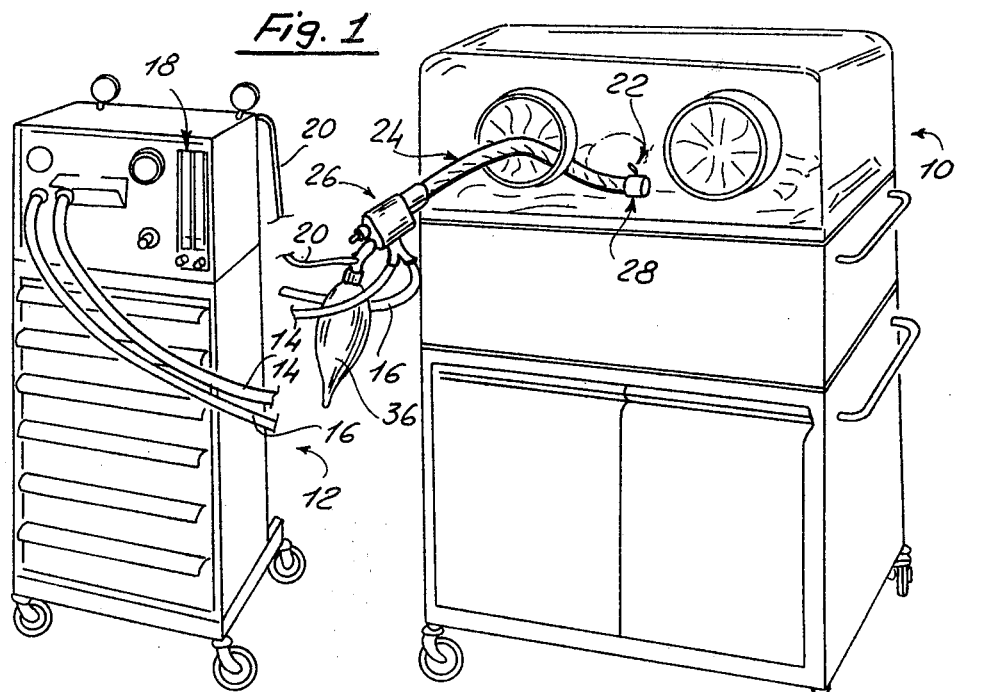
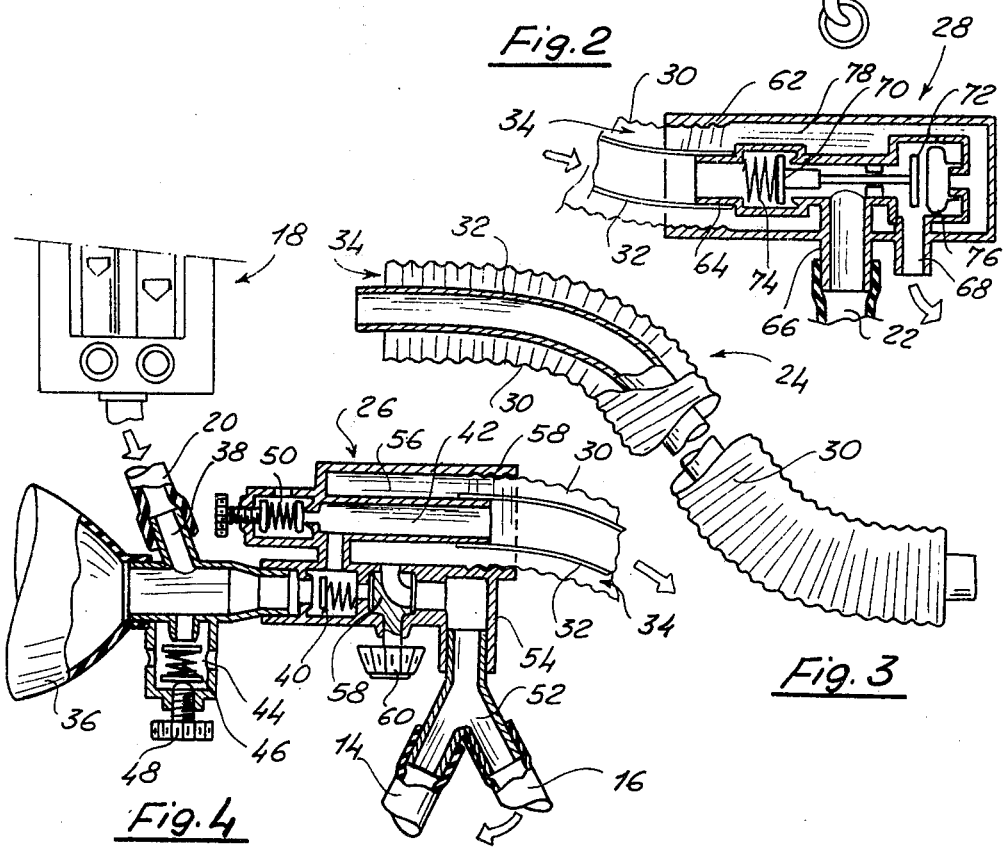

RESPIRATION SYSTEM AND DEVICE

BACKGROUND OF THE INVENTION a. The Field of the Invention

This invention is related with the art of providing and making use of respirators, that is systems and devices designed for pulsingly and forcibly introducing under appropriately slight but positive pressure through a face mask, tracheal tube or the like metered amounts of gaseous mixture into the respiratory system of a patient to expand the lungs in simulation of the normal inhalation portion of the respiratory cycle.

More particularly this invention is concerned with a new and improved respirator device of the type including a variable volume chamber having an at least partly pliable wall and confined within an enclosure having essentially rigid or unextensible walls, the space or volume internal to said variable volume chamber being connected, in operation of the device and by means of couplings, duct means and suitable check valves, with a source of slightly pressurized gaseous mixture and respectively with the patient's respiratory system.

The said variable volume chamber acts as a reciprocating pump and it is actuated by alternately applying a superatmospheric and a subatmospheric fluid generally air pressure in the interspace existing between the unextensible walls of the enclosure and the pliable wall of said chamber.

b. The Prior Art

This art is a widely known and well worked one and a variety of apparatuses for the control of respiration, resuscitation and anaesthesia have been proposed, manufactured and currently made use of. The gaseous mixture to be applied to a patient who is unable to perform satisfactory respiration without external assistance may be fresh air or oxygen enriched air as well as anesthetic or other agent containing mixture. The selection of the particular gas or mixture, of the rate, frequency and other flow parameters, and of the procedure of supplying same is the province of the physician's determination. For the purposes of this specification and in the claims, the terms "gas", "gaseous mixture" and also "gaseous volumes" will therefore be understood to mean any gaseous fluid and fluid amounts such as prescribed by the physician, together with the parameters of the respiratory pattern.

According to current art the outlet of the respirator, from which the gaseous mixture is caused to pulsingly issue, is connected to the face mask, tracheal tube or the like, by means of a tubular duct or hose, generally made of a rubbery or other pliable material, of such length to easily cover the interval between the respirator and the patient, who is sometimes enclosed into a confined thermally and atmospherically conditioned environment. Such tubular duct has a cross-sectional area such to ensure an undisturbed flow at the desired rate, without undue pressure drop. The inner volume of said duct means is therefore rather relevant and the gaseous mixture confined thereinto, at the end of any inhalation step, will be compressed but not actually supplied in the lungs of the patient. Such inner volume is generally termed "compressible volume, or space".

From the point of view of properly transferring into the patient's respiratory system the gaseous volumes for which the respirator has been adjusted, without unduly effecting the pressure, this compressible volume is a parasitic one and prejudices the correct volumetrical supplying of the prescribed gaseous volumes. The said compressible volume confined within the duct means of conventional assemblies is relevant and its measure can be of the order of one liter ($dm^3$) or more.

These noticeably large compressible volumes can be tolerated in the general case of treatment of grown-up patients and generally when substantial volumes are supplied at any breathing cycle, the prejudice of the correct supplying being a function of the ratio of the gaseous volume as a whole relatively to the compressible volume. In the field of paediatrics, and most particularly when the breathing cycle of prematurely born babies is to be ensured, the compressible volume leads to very serious problems, taking into account that the tiny respiratory systems of such patients can inhale gaseous volumes to be measured in terms of cubic centimeters. Such problems are well known to physicians and paediatrists, and to provide shorter and smaller hoses or duct means is a known expedient for decreasing the compressible volume. Such dimensional limitation of the duct means cannot however provide a completely satisfying operation, for evident reasons, in particular by the fact that the apparatus cannot be placed too close to the patient.

It is therefore a principal object of this invention to provide a new and advantageous respirator system which is not subject to the above and other limitations. More specifically, it is an object of this invention to provide a new respirator device of the type referred to above, so designed that the above discussed compressible volume will be essentially zeroed, while the source of the gaseous mixture and that of the pulsing fluid pressure can be located at a safe, substantial and undisturbing distance from the patient. The system and the device of the invention are particularly but not exclusively advantageous in the field of paediatrics, as it will be readily apparent as this description proceeds.

BRIEF SUMMARY OF THE INVENTION

According to the essential principle of the invention, the new respirator system comprises a respirator device which forms either the pumping means designed for supplying the patient with predetermined gaseous volumes upon pulsing application of suitable fluid pressure to the system, and the duct means between the sources of gaseous mixture and of the pulsing pressure, and respectively the patient.

According to more specific aspects of the invention, the new respirator device comprises an elongated tubular member having essentially unextensible walls and an essentially pliable inner dividing wall lengthwise arranged to form inside said tubular member two spaces arranged therealong for at least a substantial and preferably for the entire length of said member. One of these spaces is arranged to act as a variable volume chamber and has valve and coupling means connected thereto for connecting the said one space with the source of the gaseous mixture and with the face mask or tracheal tube and the like, and the other space is arranged to act as an interspace between the unextensible walls of the tubular member and the pliable dividing wall and has coupling means connected thereto for connecting the said other space with the source of pulsing fluid pressure which therefore promotes an alternated deformation of said pliable dividing wall and consequent alternated variation of the volume confined within said one space.

The resulting tubular structure is dimensioned for being made use of as a duct means of such length and substantial pliableness to extend, in service, from the sources of gaseous mixture and of the pulsing fluid pressure, and the said one variable volume space formed thereinto extend from end to end in said tubular structure. The said coupling and valve means comprise an inlet valve unit and an outlet valve unit each unit having coupling means designed for coupling said inlet valve unit to the said source of gaseous mixture and respectively said outlet valve unit to the said face mask or tracheal tube or the like, said units being connected to one and respectively to the opposite end portion of said tubular structure. The coupling means connected to said interspace is located at or near to the said one end of said structure, at which the said inlet valve unit is located.

Consequently, when the said tubular structure is connected and arranged for service in the complete respirator system, it is extended from the said source of gaseous mixture and of pulsing fluid pressure to the face mask or tracheal tube or the like, thus forming (a) the duct means through which the said gaseous mixture is transferred from a location satisfyingly far from the patient to a location adjacent to same patient, and (b) the respirator device by means of which the said gaseous mixture is pressurizedly, meteredly and pulsingly supplied to the patient respiratory system, the said compressible volume being essentially zeroed or, more precisely, limited to the small inner volumes of the components downstream to the outlet valve means, that is in the face mask, or in the tracheal tube or the like.

According to a preferred embodiment of the new respirator device, the variable volume chamber arranged within and along the said tubular structure consists of a thin walled hose of pliable material located lengthwise within the said unextensible tubular member and adapted for being squashed by a fluid pressure applied in the interspace formed between said thin walled hose and said tubular member. This latter member preferably consists of a fabric reinforced rubber hose.

According to another preferred feature of the invention, the said outlet valve unit comprises a three-way distributing valve, or fluid switch, connected for selectively connecting the said face mask, or tracheal tube or the like, that is the patient's respiratory system, to the adjacent end portion of the elongated variable volume chamber and respectively to an exhaust outlet, during the inhalation and the exhalation portions of the respiratory pattern. The said fluid switch is actuated by a pressure sensitive actuator connected to sense the pulsing pressure when "on" and applied into said interspace for connecting said variable volume chamber with the patient's respiratory system and respectively for connecting said latter system with the exhaust outlet when said pulsing pressure is in "off" phase and therefore temporarily discontinued in said interspace, whereby a respiratory pattern effectively governed by the cycle of the source of pulsing pressure, according to the adjustment at physician's determination, is provided.

These and other objects, features and advantages of the new respiratory device will be made apparent from the following detailed description of a preferred embodiment thereof, said description being referred to the accompanying drawings.

THE SEVERAL VIEWS OF THE DRAWING

FIG. 1 is a diagrammatical perspective view of a complete respiration system including the new respiration device, in service;

FIGS. 2, 3 and 4 are somewhat simplified longitudinal sectional views and partly side elevation views of the outlet and respectively of the middle and of the inlet portions of the device during the inhalation portion of the respiratory pattern;

DETAILED DESCRIPTION OF THE PREFERRED EMBODIMENT

Figure 5:
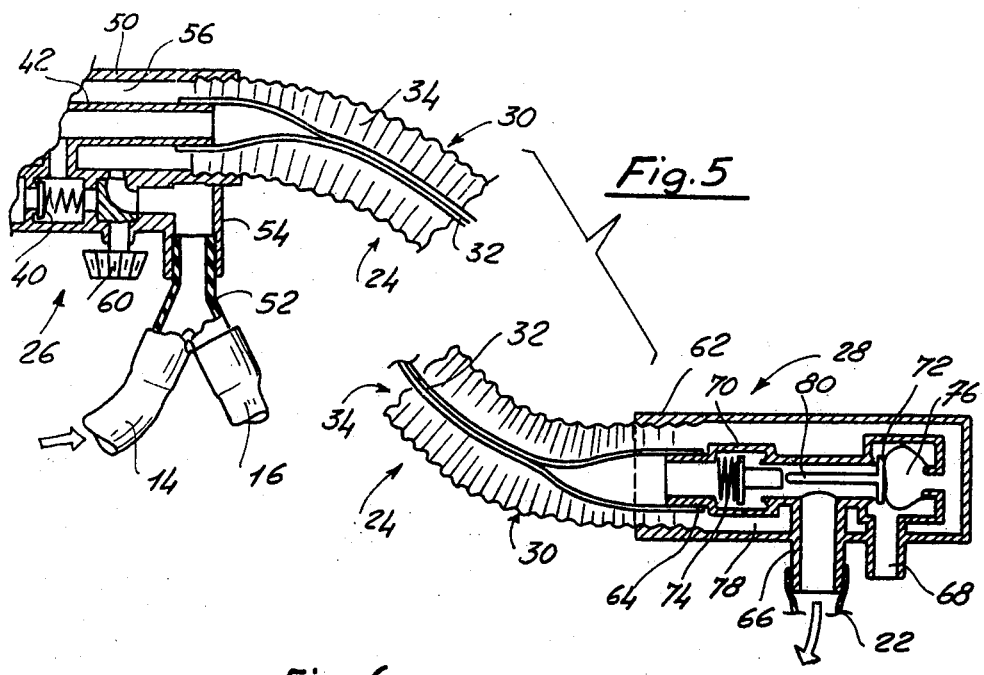
FIG. 5 is a similar view in which the portions of FIGS. 2 and 4 are illustrated during the exhalation portion of said pattern.

Referring first to FIG. 1, there is shown a respiration system in service for assisting the breathing cycle of a prematurely or a new born accomodated within a known thermally conditioned cradle, generally indicated at 10. The respiration device is connected to and actuated by a suitable known apparatus, indicated at 12, having conventionally arranged and supplied hoses 14 and 16 through which positive and respectively negative fluid pressure, that is pressurized air (or other gas) and respectively a suction is applied to the respirator device, according to a cycle the frequency and the other parameters of which are assumed to have been adjusted at physician's determination. The apparatus comprises further a source of slightly pressurized gaseous mixture of proper composition and humidity to be supplied to the body patient, through known rate of flow and composition control means, generally indicated at 18, a hose 20, the new respiration device, and a tracheal tube 22, for example.

In its broadest aspect, the said new respirator device comprises an elongated, generally pliable tubular structure 24, a "far" (from the patient) inlet valve and coupling unit 26, and a "near" (to the patient) outlet valve and coupling unit 28. As shown in FIG. 1, the respirator device forms, in the respirator system, a subassembly which, apart from its specific operation and features, approximately corresponds to and is substitutive of the conventional hose through which the gaseous mixture is usually pulsingly supplied from a well far respiration system to a patient, and wherein a relevant compressible volume or space exists.

The principal specific features of the said device 24–28 are shown in FIGS. 2 to 5. The tubular structure 24 comprises an outer tubular member 30 and an inner thin and pliable walled hose 32 of diameter less than that of the member 30, so that an interspace 34 is formed and maintained between said tubular components. The outer tubular member has generally pliable but essentially unextensible walls to confine a not variable overall volume thereinto. Such member 30 may consist of a fabric reinforced corrugated rubber pipe, for example. The inner hose or tube may consist of a thin walled rubber or polyethylene pipe of such pliableness to be flattened when a pressure, such as the actuating pulsing pressure has been applied about, as provided by the said respirator apparatus 12, or by squeezing a rubber balloon, or another hand manipulated device such as a bellow or accordion type collapsible hand squeezable hollow body.

The inlet or "far" valve unit 26 comprises a pipe fitting 38 for coupling it with the gaseous mixture supply hose 20, from which the mixture is transferred, via a check valve 40 and another pipe fitting 42, to the inlet end portion of the inner tube 32, fitted about such fitting 42. A spring biased relief valve 44 is provided for exhausting, if necessary, amounts of supplied gaseous mixture in excess to that actually delivered to the patient. The load of the biasing spring 46 can be adjusted by rotating a knob 48 connected to a known screw arrangement on which such spring abuts. The inlet passage for the gaseous mixture is further connected with a hand squeezable balloon 36 for applying an extra pressure to the gaseous mixture, in emergencies. Further, a pressure relief valve biased by a spring 50, the bias of which can also be adjusted by a similar screw and knob arrangement, is provided for relieving the gaseous mixture pressure if an overresistance is encountered.

The inlet valve and coupling unit 26 has also passage and coupling means for connecting the respiration device to the source of the actuating pulsing fluid pressure. These means comprise a known Y-shaped pipe fitting 52 having two inlets for connection to the said hoses 14 and 16 from apparatus 12 (FIG. 1) and an outlet fitted into a pipe socket 54 connected to an outer space 56 integrally formed in the body 58 of the unit 26, co-axial to the fitting 42, and in which the inlet portion of the outer tubular member 30 is secured. Therefore, the pulsing positive or negative pressure from hoses 14 and 16, as provided by the apparatus 12, is applied in the interspace existing between the tubular components 30 and 32 of the tubular structure 24, for providing the operational cycle of the device, including inhalation portions during which the inner hose 32 is squashed by positive pressure in said interspace and exhalation portions during which the negative pressure, in same interspace, allows the same hose to be inflated again by the slightly pressurized gaseous mixture continuously supplied thereto.

A switch 58 provided with a knob 60 is also provided for discontinuing the communication between the socket 54 and the outer space 56, and placing such space 56 in communication either with the hand squeezable balloon 36 and with the source of slightly pressurized gaseous mixture, from hose 20. Such arrangement is useful in emergencies and when an apparatus such as at 12 is not available. An amount of gaseous mixture will in such occurrence fill the interspace between the tubular components 30 and 32 and can be alternatively pressurized and depressurized by hand manipulation of balloon 36. This manipulation is well known to physicians and does not form part of the invention.

The outlet or near (to the patient) valve coupling unit 28 comprises an outer socket 62 and an inner socket 64 for fitting of the opposite end portions of the outer tubular member 30 and respectively of the inner thin walled hose 32. The inner socket 64 forms the inlet of a passage having outlets 66 and 68 connected thereto and including a pressure controlled valve 70 upstream of both said outlets, biased by a spring 74 and associated with a second valve member 72 upstream of the outlet 68. The outlet 66 is designed to be coupled to the patient's respiratory system, by means of a face mask, or a tracheal tube 22 (fragmentarily shown in FIGS. 2 and 5 or the like. The outlet 68 acts as an exhaust for the exhalated gases, and it is indicated by a phantom outline in FIG. 6.

A small inflatable bell or balloon 76 is located in front of valve member 72 and its inner space is connected, through passages 78, to the interspace 34 between the tubular member 30 and the inner hose 32 and designed to urge, when inflated by a fluid pressure, the second valve member 72 in sealing abutment against its associated valve seat and concurrently opening the passage at the valve 70, against the bias provided by spring 74.

Upon a consideration and comparison of FIGS. 2–4 and 5 the operation of the described respiration device will be readily understood. Assuming first that the patient is performing the exhalation portion of his breathing cycle, no or a slightly negative pressure will be applied by the known apparatus 12 in the interspace 34. The small bell 76 (FIG. 2) will remain deflated so that valve 72 will be open and valve 70 will be closed by the bias of spring 74. No gaseous mixture can reach the outlet 66, that is the patient, while the exhalated gases from the tracheal tube 22 (or face mask or the like) will be exhausted through the outlet 66, the open valve 72 and the outlet 68. If desired, said outlet 68 can be connected to a hose for exhausting the exhalate outside of the space of the cradle 10 and also, if required, for connecting such outlet 68 with a source of slight underatmospheric pressure to assist the exhalation portion of the cycle.

In the meantime, the gaseous mixture delivered by hose 20 (FIG. 4) at a slight overatmospheric pressure, enters through the fitting 38, valve 40 and fitting 42, into the inner thin walled hose or tube 32, inflating it for its overall length up to the closed valve 70 in the outlet or near valve unit. This inflation is not disturbed or opposed because no positive pressure about the inner hose exists (in interspace 34). The various movable components are set as shown in FIGS. 2 to 4.

Assuming now that the device is being operating for forcing or assisting an inhalation portion of the patient's breathing cycle, this step is governed by a fluid pressure pulse delivered by the apparatus 12, through the hose 14. The pressure will be transferred, through fittings 52 and 54, switch valve 58 and outer passage 56, in the interspace 34, which will be therefore pressurized. This pressurization leads to two concurring effects:

a. the pressure will reach, through the passages 78, the inflatable bell 76 and will inflate it. The bell will thus urge the valve 72 to close (thus closing any passage between the patient and the exhaust) and the valve 70 to open;

b. the pressure about the inner thin walled hose 32 will squash it (FIG. 5). The volume of the gaseous mixture, which has previously inflated such hose, will be forced thereoff in the patient's respiratory system, through the fitting or socket 64, the now open valve 70, outlet 66 and tracheal tube 22 (or face mask or the like). Said volume cannot return towards the source of the gaseous mixture as being halted by the valve 40 which acts as a check valve. Any excess of such volume which cannot be actually inhaled, if any, will be exhausted through the pressure relief valve 50 (FIG. 4). The inner hose 32 will be squashed until very near to the outlet or near valve unit 28 and therefore no noticeable compressible space or volume is formed during the operation.

It is believed that the rather simplified illustration of the various principal components of the new device and their cooperation, as shown in FIGS. 2 to 5, will enable those skilled in the art to fully understand, make and use the invention. Certain structural details of a preferred embodiment of the outlet or near (to the patient) unit 28 are however illustrated in the detailed and enlarged view of FIG. 6.

Figure 6:
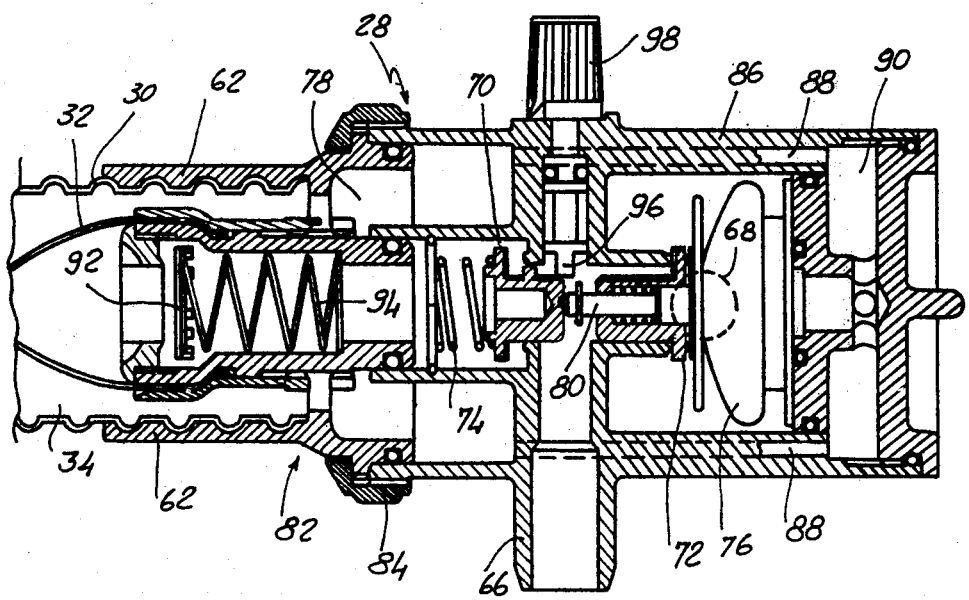
FIG. 6 is an enlarged and detailed view of the outlet valve unit including pressure responsible actuator means.

In such FIG. 6 there is shown the fitting of the outlet ends of member 30 and of hose 32 inside and about co-axial and tubular portions (forming the sockets) of a sleeve 82 which is detachably connected, such as by screwing at 84, to the body 86 of the unit 28. The inner passage of such sleeve includes also a check valve 92 slightly biased by a spring 94 and acting as a safety in the occurrence of not proper operation of the pressure sensitive and operated valves 70 and 72, the latter acting on the former through a stem 80. The passage 78, which forms the end portion of the interspace 34, is connected to the inside of the inflatable bell 76 by means of a plurality of passages 88 bored into a thick walled part of said body 86, from said passage 78 to a rear chamber 90.

The unit 28 is further advantageously provided with an ancillary device, diagrammatically shown at 96 and connected to a knob 98, for example, including a cam or dog means adapted for positively disabling the pressure actuated valves 70 and 72, by fixedly closing valve 70 and amply opening valve 72, for enabling the patient to perform spontaneous respiration.

I claim:

1. In a device for administering a gaseous medium from a remotely located source to a patient, a combination, comprising elongated, bendable but shape-retaining tubular means having one end arranged adjacent the patient and its other end spaced therefrom and adapted to communicate with said source, said tubular means including an inner, flexible collapsible first tube bounding an interior space and an outer, bendable but shape-retaining second tube surrounding said first tube and defining a pumping chamber therewith; inlet means at said other end and having an inlet port in communication with said source of gaseous medium to be conveyed to the patient and with said interior space; outlet means at said one end communicating with said interior space and having an outlet port adapted to be in communication with the patient; and pumping means in communication with said pumping chamber and with an alternately-cycled source of pressurized medium for intermittently compressing said flexible first tube and thereby pumping during each compression a quantity of the gaseous medium therein via said inlet means towards said outlet means and from there to the patient.

2. The combination as defined in claim 1, wherein said inlet means further comprises a valve member movable between an open and a closed position to permit the gaseous medium to flow towards but not from said interior space, and pressure-relief valve means exposed to the gaseous medium in said interior space for relieving the pressure of the gaseous medium contained therein.

3. The combination as defined in claim 1; and further comprising a compressible balloon-shaped element constituting an additional alternately-cycled source of pressurized medium, said balloon-shaped element having its interior in communication with said inlet port; and further comprising a switching element movable between a normal first position in which said pumping chamber communicates with said first-mentioned alternately-cycled source and a second position in which said pumping chamber communicates with said additional alternately-cycled source of pressurized medium.

4. The combination as defined in claim 1, wherein said outlet means further comprises an exhaust port for discharging the exhaust medium exhaled by the patient.

5. The combination as defined in claim 4, wherein said outlet means further comprises valve means movable between a first inspiratory position in which said interior space is opened to permit communication of said quantity of gaseous medium therein with the patient and in which said exhaust port is closed to prevent said quantity of gaseous medium from flowing towards and thereby escaping therefrom, and a second normal expiratory position in which said exhaust port is opened to permit communication of the exhaust medium therewith and in which said interior space is closed to prevent the exhaust medium from flowing towards and thereby entering said interior space.

6. The combination as defined in claim 5; and further comprising pressure-sensitive means exposed to and in communication with the pressurized medium in said pumping chamber for moving said valve means between said first and second positions in response to the pressures generated by said alternately-cycled source of pressurized medium.

7. A device as claimed in claim 6, wherein said pressure sensitive means comprises a pressure inflatable hollow body and passage means connecting the interior of said body to said pumping chamber.

8. The combination as defined in claim 6, wherein said pressure-sensitive means comprises a resilient, hollow element having its interior in communication with the pressurized medium and being located adjacent said valve means, said element being inflatable towards a first expanded size in which said valve means is moved towards its first inspiratory position and being deflatable towards a second unexpanded size in which said valve means assumes its second normal expiratory position.

9. The combination as defined in claim 5, wherein said valve means comprises a pair of valves axially spaced from each other on a common rod.

10. The combination as defined in claim 5, and further comprising locking means for maintaining said valve means in said second expiratory position.

* * * * *